US00PP22882P2

(12) United States Plant Patent
Isobe et al.

(10) Patent No.: US PP22,882 P2
(45) Date of Patent: Jul. 24, 2012

(54) ***PETUNIA* PLANT NAMED 'SUNSURFKIRO'**

(50) Latin Name: *Petunia×hybrida*
Varietal Denomination: Sunsurfkiro

(75) Inventors: Yasuko Isobe, Shiga (JP); Takeshi Kanaya, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 10 days.

(21) Appl. No.: 12/930,055

(22) Filed: Dec. 24, 2010

(51) Int. Cl.
*A01H 5/00* (2006.01)

(52) U.S. Cl. ..... Plt./356.15

(58) Field of Classification Search ..... Plt./356.15
See application file for complete search history.

*Primary Examiner* — Susan McCormick Ewoldt
(74) *Attorney, Agent, or Firm* — C. A Whealy

(57) ABSTRACT

A new and distinct cultivar of *Petunia* plant named 'Sunsurfkiro', characterized by its upright and outwardly spreading plant habit; vigorous growth habit; freely branching; freely flowering habit; long flowering period; medium-sized white-colored flowers with yellow green-colored venation; and good garden performance.

1 Drawing Sheet

Botanical designation: *Petunia×hybrida*.
Cultivar denomination: 'SUNSURFKIRO'.

BACKGROUND OF THE INVENTION

The present invention relates to a new and distinct cultivar of *Petunia* plant, botanically known as *Petunia×hybrida* and hereinafter referred to by the name 'Sunsurfkiro'.

The new *Petunia* plant is a product of a planned breeding program conducted by the Inventors in Higashiomi, Shiga, Japan. The objective of the breeding program is to create new upright and outwardly spreading *Petunia* plants with freely branching habit and attractive flower coloration.

The new *Petunia* plant originated from a cross-pollination made by the Inventors in April, 2005 in Higashiomi, Shiga, Japan of a proprietary selection of *Petunia×hybrida* identified as code number PF104-1, not patented, as the female, or seed, parent with a proprietary selection of *Petunia×hybrida* identified as code number 02916, not patented, as the male, or pollen, parent. The new *Petunia* plant was discovered and selected by the Inventors as a single flowering plant within the progeny of the stated cross-pollination in a controlled environment in Higashiomi, Shiga, Japan in September, 2006.

Asexual reproduction of the new *Petunia* plant by terminal cuttings in a controlled environment in Higashiomi, Shiga, Japan since October, 2006, has shown that the unique features of this new *Petunia* plant are stable and reproduced true to type in successive generations.

SUMMARY OF THE INVENTION

Plants of the new *Petunia* have not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Sunsurfkiro'. These characteristics in combination distinguish 'Sunsurfkiro' as a new and distinct cultivar of *Petunia:*

1. Upright and outwardly spreading plant habit.
2. Vigorous growth habit.

3. Freely branching.
4. Freely flowering habit.
5. Long flowering period.
6. Medium-sized white-colored flowers with yellow green-colored venation.
7. Good garden performance.

Plants of the new *Petunia* can be compared to plants of the female parent selection. Plants of the new *Petunia* differ primarily from plants of the female parent selection in the following characteristics:

1. Plants of the new *Petunia* are more freely branching than plants of the female parent selection.
2. Plants of the new *Petunia* have smaller flowers than plants of the female parent selection.
3. Petal apices of plants of the new *Petunia* are acute whereas petal apices of plants of the female parent selection are rounded.

Plants of the new *Petunia* can be compared to plants of the male parent selection. Plants of the new *Petunia* differ primarily from plants of the male parent selection in the following characteristics:

1. Plants of the new *Petunia* have larger flowers than plants of the male parent selection.
2. Plants of the new *Petunia* and the male parent selection differ in flower color as plants of the male parent selection have white-colored flowers.
3. Petal apices of plants of the new *Petunia* are acute whereas petal apices of plants of the male parent selection are rounded.

Plants of the new *Petunia* can also be compared to plants of the *Petunia* 'KEIyeul', disclosed in U.S. Plant Pat. No. 13,968. In side-by-side comparisons conducted in Higashiomi, Shiga, Japan, plants of the new *Petunia* and 'KEIyeul' differed primarily in the following characteristics:

1. Plants of the new *Petunia* were not as trailing and broad as plants of 'KEIyeul'.
2. Plants of the new *Petunia* had shorter internodes than plants of 'KEIyeul'.
3. Plants of the new *Petunia* had smaller leaves than plants of 'KEIyeul'.

4. Plants of the new *Petunia* had smaller flowers than plants of 'KElyeul'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the top of the sheet comprises a side perspective view of a typical flowering plant of 'Sunsurfkiro' grown in a container.

The photograph at the bottom of the sheet is a close-up view of a typical flowering plant of 'Sunsurfkiro'.

DETAILED BOTANICAL DESCRIPTION

The aforementioned photographs and following observations, measurements and values describe plants grown during the spring and early summer in 15-cm containers in an outdoor nursery in Higashiomi, Shiga, Japan and under commercial practices. During the production of the plants, day temperatures averaged 23° C. and night temperatures averaged 13° C. Plants were four months old when the photographs and description were taken. In the following description, color references are made to The Royal Horticultural Society Colour Chart, 2001 Edition, except where general terms of ordinary dictionary significance are used.

Botanical classification: *Petunia×hybrida* 'Sunsurfkiro'.

Parentage:

*Female, or seed, parent*.—Proprietary selection of *Petunia×hybrida* identified as code number PF104-1, not patented.

*Male, or pollen, parent*.—Proprietary selection of *Petunia×hybrida* identified as code number 02916, not patented.

PROPAGATION:

*Type*.—By terminal cuttings.

*Time to initiate roots*.—About one week at temperatures of 15° C. to 20° C.

*Time to produce a rooted young plant*.—About three weeks at temperatures of 15° C. to 20° C.

*Root description*.—Fibrous; white in color.

*Rooting habit*.—Freely branching.

Plant description:

*Plant and growth habit*.—Upright and outwardly spreading plant habit; freely branching habit with numerous lateral branches developing per plant; pinching enhances lateral branch development; vigorous growth habit.

*Plant height*.—About 18.9 cm.

*Plant diameter*.—About 39.5 cm.

Lateral branch description:

*Length*.—About 18.5 cm.

*Diameter*.—About 2.4 mm.

*Internode length*.—About 1.2 cm.

*Strength*.—Strong, flexible.

*Aspect*.—Upright to outwardly.

*Texture*.—Pubescent.

*Color*.—Close to 146B.

Foliage description:

*Arrangement*.—Alternate, simple.

*Length*.—About 4.2 cm.

*Width*.—About 1.8 cm.

*Shape*.—Narrowly elliptic.

*Apex*.—Acute.

*Base*.—Cuneate.

*Margin*.—Entire.

*Texture, upper and lower surfaces*.—Pubescent.

*Venation pattern*.—Pinnate; reticulate.

*Color*.—Developing and fully expanded leaves, upper surface: Close to 137C; venation, close to 145B. Developing and fully expanded leaves, lower surface: Close to 144B; venation, close to 145B.

*Petioles*.—Length: About 6.2 mm. Diameter: About 3.1 mm. Texture, upper and lower surfaces: Pubescent. Color, upper and lower surfaces: Close to 145B.

Flower description:

*Flower arrangement and habit*.—Single salverform flowers arising from leaf axils; freely flowering habit with usually about 31 open flowers per plant; flowers face upright to outwardly.

*Fragrance*.—None detected.

*Natural flowering season*.—Early flowering habit, plants of the new *Petunia* initiate and develop flowers about three to four weeks after planting; long flowering period; flowering commences naturally during the spring and plants flower continuously throughout the summer until late autumn in Japan.

*Flower longevity*.—Individual flowers last about seven to ten days on the plant; flowers not persistent.

*Flower diameter*.—About 5.7 cm.

*Flower length (depth)*.—About 4.3 cm.

*Throat diameter*.—About 10.7 mm.

*Tube diameter, base*.—About 3 mm.

*Tube length*.—About 2.7 cm.

*Flower bud*.—Shape: Cylindrical. Length: About 3.6 cm. Diameter: About 1.2 cm. Color: Close to N144D.

*Corolla*.—Arrangement: Five petals fused at the base and opening into a flared trumpet. Petal length from throat: About 2.5 cm. Petal width: About 2.5 cm. Petal shape: Spatulate. Petal apex: Acute. Petal margin: Entire. Petal texture, upper and lower surfaces: Smooth, glabrous. Throat texture: Smooth, glabrous. Tube texture: Pubescent. Color: Petal, when opening, upper surface: Close to NN155A; mid-vein, close to N144A; lateral venation, close to 151C to 151D. Petal, when opening, lower surface: Close to 150D. Petal, fully opened, upper surface: Close to NN155A; mid-vein, close to N144A; lateral venation, close to 151C to 151D. Petal, fully opened, lower surface: Close to 4D. Throat: Close to 7A to 7C. Tube: Close to 4C to 4D.

*Calyx*.—Arrangement: One star-shaped calyx tube with five sepals fused at the base per flower. Sepal length: About 1.1 cm. Sepal width: About 3.2 mm. Sepal shape: Elliptic. Sepal apex: Obtuse. Sepal margin: Entire. Sepal texture, upper and lower surfaces: Pubescent. Color, immature and mature, upper surface: Close to 137D. Color, immature and mature, lower surface: Close to 144B.

*Peduncles*.—Length: About 1.9 cm. Diameter: About 1.9 mm. Strength: Strong. Texture: Pubescent. Color: Close to 146B.

*Reproductive organs*.—Stamens: Quantity/arrangement: Five per flower. Stamen length: About 2.1 cm. Anther shape: Ellipsoidal. Anther size: About 2.6 mm by 2.1 mm. Anther color: Close to 12D. Pollen amount: Moderate. Pollen color: Close to 13D. Pistils: Quantity: One per flower. Pistil length: About 2.2 cm. Style color: Close to 145C. Stigma shape: Transversely ellipsoidal. Stigma color: Close to 143B. Ovary color: Close to 144A. Seeds/fruits: Seed and fruit development have not been observed on plants of the new *Petunia*.

Garden performance: Plants of the new *Petunia* have been observed to have good garden performance and to tolerate rain, wind and temperatures ranging from about 5° C. to about 35° C.

Pathogen/pest resistance: Plants of the new *Petunia* have not been observed to be resistant to pathogens and pests common to *Petunia* plants.

It is claimed:

1. A new and distinct *Petunia* plant named 'Sunsurfkiro' as illustrated and described.

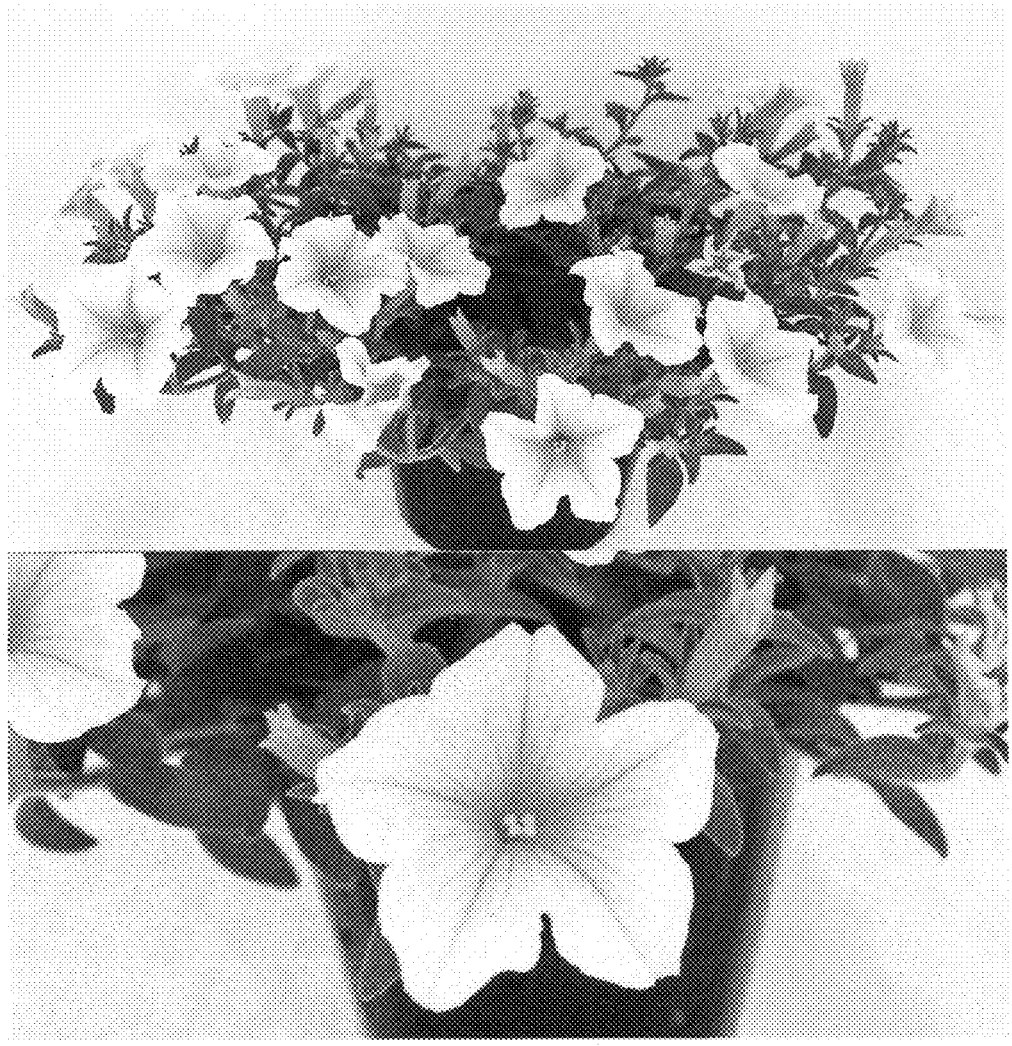

* * * * *